US011735682B2

(12) United States Patent
Ruegheimer et al.

(10) Patent No.: US 11,735,682 B2
(45) Date of Patent: Aug. 22, 2023

(54) SEMICONDUCTOR DEVICE

(71) Applicant: OSRAM OLED GmbH, Regensburg (DE)

(72) Inventors: Tilman Ruegheimer, Regensburg (DE); Hubert Halbritter, Dietfurt (DE)

(73) Assignee: OSRAM OLED GmbH, Regensburg (DE)

( * ) Notice: Subject to any disclaimer, the term of this patent is extended or adjusted under 35 U.S.C. 154(b) by 372 days.

(21) Appl. No.: 16/754,612

(22) PCT Filed: Oct. 16, 2018

(86) PCT No.: PCT/EP2018/078253
§ 371 (c)(1),
(2) Date: Apr. 8, 2020

(87) PCT Pub. No.: WO2019/076900
PCT Pub. Date: Apr. 25, 2019

(65) Prior Publication Data
US 2020/0287072 A1    Sep. 10, 2020

(30) Foreign Application Priority Data
Oct. 18, 2017   (DE) .................... 10 2017 124 319.4

(51) Int. Cl.
*H01L 31/173*   (2006.01)
*G01S 17/04*    (2020.01)
(Continued)

(52) U.S. Cl.
CPC .......... *H01L 31/173* (2013.01); *G01S 7/4815* (2013.01); *G01S 17/04* (2020.01);
(Continued)

(58) Field of Classification Search
CPC ... A61B 5/02427; G01S 7/4815; G01S 7/481; H01L 25/167; H01L 27/14
See application file for complete search history.

(56) References Cited

U.S. PATENT DOCUMENTS 8,822,925 B1 *  9/2014  Patel ..................... G06F 1/3231
                                                              250/341.5
9,368,683 B1    6/2016  Meitl et al.
(Continued)

FOREIGN PATENT DOCUMENTS

DE   10 2017 124 321 A1   4/2019
EP       3 211 453 A1      8/2017
(Continued)

OTHER PUBLICATIONS

Japanese Decision of Rejection dated Jan. 4, 2022, of corresponding Japanese Patent Application No. 2020-518777, along with English.
(Continued)

*Primary Examiner* — Yuzhen Shen
(74) *Attorney, Agent, or Firm* — DLA Piper LLP (US)

(57) ABSTRACT

A semiconductor device includes a first semiconductor body including a substrate having a first thickness, wherein the first semiconductor body includes a first active zone that generates or receives radiation, and a second semiconductor body having a second thickness smaller than the first thickness and including a tear-off point is arranged on the substrate and connected in an electrically conducting manner to the first semiconductor body, wherein the second semiconductor body includes a second active zone that generates or receives radiation, and the second active zone generates radiation and the first active zone detects the radiation, and the first semiconductor body includes contacts on its underside for connection to the semiconductor device.

10 Claims, 4 Drawing Sheets

(51) Int. Cl.
*G01S 7/481* (2006.01)
*H01L 25/16* (2023.01)
*A61B 5/024* (2006.01)
*G06F 3/01* (2006.01)

(52) U.S. Cl.
CPC ........ *H01L 25/167* (2013.01); *A61B 5/02427* (2013.01); *G06F 3/017* (2013.01)

(56) References Cited

U.S. PATENT DOCUMENTS

| | | |
|---|---|---|
| 2004/0222357 A1 | 11/2004 | King et al. |
| 2010/0200898 A1 | 8/2010 | Lin et al. |
| 2010/0219733 A1 | 9/2010 | Wan et al. |
| 2011/0108860 A1 | 5/2011 | Eissler et al. |
| 2013/0208026 A1 | 8/2013 | Takahito et al. |
| 2014/0231635 A1* | 8/2014 | Kerness ............ H01L 31/02325 250/226 |
| 2016/0306042 A1* | 10/2016 | Schrank .............. H01L 27/1443 |
| 2016/0336488 A1 | 11/2016 | Bower et al. |
| 2017/0133818 A1 | 5/2017 | Cok |
| 2017/0287882 A1* | 10/2017 | Cok ........................ H01L 25/50 |
| 2017/0287886 A1* | 10/2017 | Gani ..................... H01L 23/481 |
| 2018/0006182 A1* | 1/2018 | Renard ................. G01S 7/4813 |
| 2018/0342654 A1* | 11/2018 | Chen ..................... H01L 33/483 |

FOREIGN PATENT DOCUMENTS

| | | |
|---|---|---|
| JP | 2006-310563 A | 11/2006 |
| JP | 2009-010048 A | 1/2009 |
| JP | 2011-521462 A | 7/2011 |
| JP | 2013-165170 A | 8/2013 |
| JP | 2017-504959 A | 2/2017 |
| WO | 2009/095860 A1 | 8/2009 |

OTHER PUBLICATIONS

Notice of Reason(s) for Rejection dated Apr. 20, 2021, of counterpart Japanese Patent Application No. 2020-518777, along with an English translation.

Bower, C. A. et al., "Emissive displays with transfer-printed assemblies of 8μm–15μm inorganic light-emitting diodes," *Photonics Research*, 2017, vol. 5, No. 2, pp. A23-A29.

OSRAM Opto Semiconductors GmbH, Datasheet SFH 7779, "Ambient Light and Proximity Sensor with Integrated 940nm IR Emitter," 2014, Version 1.0, pp. 1-34.

OSRAM Opto Semiconductors GmbH, Datasheet SFH7050, "BioMon Sensor," 2016, Version 1.1, pp. 1-23.

First Office Action dated Mar. 10, 2023, of counterpart Chinese Patent Application No. 201880068187.5, along with a machine translation in English.

* cited by examiner

SEMICONDUCTOR DEVICE

TECHNICAL FIELD

This disclosure concerns a semiconductor device and the use of such a device.

BACKGROUND

Optical sensors may comprise a combination of one or more emitters and one or more receivers and a measuring section. The receivers detect radiation emitted by the emitters after passing through the measuring section. Based on the detected value, an environmental property can be quantitatively or qualitatively measured. The radiation is usually light in the visible and/or non-visible range. An optical sensor that detects to what extent the emitted light is reflected is called a reflective sensor.

Optical sensors are used, for example, in smartphones in which the display darkens as soon as the device is brought to the head. For this purpose, a chip emitting in the infrared based on the AlGaAs material system emits light, and a silicon-based detector detects the backscattered light, from which the distance to the head can be deduced. Usually, the silicon chip has a larger area than the light-emitting chip.

Such sensors are based on integration of singulated emitter and receiver chips at a package level. Usually, arrangements with housing and printed circuit board (PCB) as are used with chips, also denoted as PCB-based packages, which allow design flexibility and low costs. During production, the chips to be integrated are mounted on the circuit board, e.g. bonded. Then, optical elements such as barriers, lenses and/or filters are added. During production, all chips and optical elements are mounted sequentially on the circuit board.

The typical thickness of circuit boards used for such sensors is about 200 μm. Typical chip thicknesses are about 100-150 μm. The overall height of the component also includes further optical elements, e.g. frames to avoid crosstalk, as well as provisions for bonding wires, potting and the like.

Such sensors are used, for example, for the measurement of heart rate and/or blood oxygen saturation as well as proximity or ambient light sensor.

There is nonetheless a need to provide a flatter device.

SUMMARY

We provide a semiconductor device including a first semiconductor body including a substrate having a first thickness, wherein the first semiconductor body includes a first active zone that generates or receives radiation, and a second semiconductor body having a second thickness smaller than the first thickness and including a tear-off point is arranged on the substrate and connected in an electrically conducting manner to the first semiconductor body, wherein the second semiconductor body includes a second active zone that generates or receives radiation, and the second active zone generates radiation and the first active zone detects the radiation, and the first semiconductor body includes contacts on its underside for connection to the semiconductor device.

We also provide a sensor including a semiconductor device including a first semiconductor body including a substrate having a first thickness, wherein the first semiconductor body includes a first active zone that generates or receives radiation, and a second semiconductor body having a second thickness smaller than the first thickness and including a tear-off point is arranged on the substrate and connected in an electrically conducting manner to the first semiconductor body, wherein the second semiconductor body includes a second active zone that generates or receives radiation, and the second active zone generates radiation and the first active zone detects the radiation, and the first semiconductor body includes contacts on its underside for connection to the semiconductor device, wherein the sensor is a proximity, gesture, heart rate or body function sensor.

Figure 1:
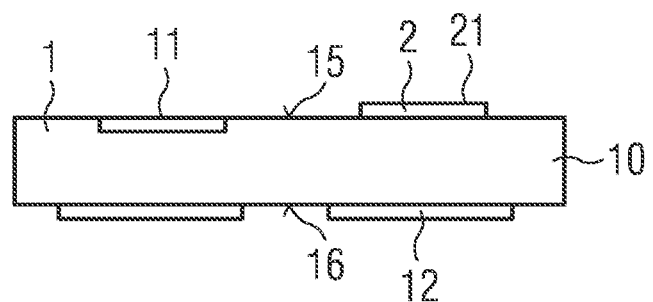
FIG. 1 shows a schematic view of an example of a semiconductor device.

REFERENCE SIGN 1, 2 semiconductor body
10 substrate
11, 21 active zone
12, 23 contacts
15 top side
16 underside
18 optical barrier
19 depression
22 conductive layer
24 mirrored sidewall
30 holding structure
32 web
34 anchor structure
38 extension
40 tear-off point
52 sacrificial wafer
54 target wafer

DETAILED DESCRIPTION

Our semiconductor device comprises a first semiconductor body having a substrate that has a first thickness, and a second semiconductor body that has a second thickness smaller than the first thickness, comprises a tear-off point, is arranged on the substrate and connected in an electrically conducting manner to the first semiconductor body.

A semiconductor body is an integrated circuit applied to a carrier material, the integrated circuit comprising an assembly or only a single component, e.g. an LED. Such a semiconductor body can also be called a chip.

The first semiconductor body comprises the substrate in or on which the integrated circuit is applied, for example, by a structured layer sequence. The first semiconductor body can be a silicon chip. The substrate also serves as a carrier for the second semiconductor body. It is not necessary to place it directly on the substrate, but it can also be mounted on the layers or structures arranged thereon. Even after the second semiconductor body has been placed, further structured layers can be applied to the first and also the second semiconductor body. The first thickness is advantageously equal to or less than 200 µm, especially 100-200 µm. The second thickness is only a few microns.

The second semiconductor body comprises a tear-off point resulting from the production process in which the second semiconductor bodies are produced in an assemblage so that the second semiconductor bodies still connected to each other are connected to each other via holding structures extending to the second semiconductor bodies and form an assemblage. The connection area between the actual semiconductor body and the holding structures is small compared to the semiconductor body and allows the semiconductor body to be easily torn away from the holding structures. The second semiconductor body may comprise a web-shaped extension, originating from the connection with the holding structure, having the tear-off point at its end.

Separation of the second semiconductor body from the holding structures is carried out during a mounting step in which the second semiconductor body is picked up by an elastomer stamp, torn off and placed on the first semiconductor body with the stamp. This step is carried out while the first semiconductor bodies are still in the wafer assemblage, in parallel for several semiconductor bodies with a stamp that simultaneously picks up several second semiconductor bodies and then places them in their positions on the first semiconductor bodies so that this process step is also called a parallel placement process. Due to the similarity to a printing process, the parallel placement process briefly described above is also referred to as "(Micro-)Transfer-Printing".

The first semiconductor body may comprise a first active zone that generates radiation or receives radiation, and the second semiconductor body may comprise a second active zone that generates radiation or receives radiation. This allows use of the second active zone to generate radiation and the first active zone to detect it to design the semiconductor device as a reflective sensor. The radiation is emitted from the top side of the semiconductor device, reflected on the measuring section and the portion of radiation reflected back to the top side is detected. For this purpose, the semiconductor device is shaped such that the first active zone is arranged at a top side of the first semiconductor body and the second semiconductor body is also arranged on or at the top side.

Such a sensor differs from a conventional sensor in that, instead of mounting the individual chips on a circuit board, one of the chips is used as a carrier for the others. This is usually the largest (silicon-) chip in terms of area. In other words, the semiconductor body that has the integrated circuit or active zone with the largest spatial extent also serves as a carrier for other semiconductor bodies. Both a silicon technology with integrated electronics, e.g. amplifier circuit, digitization, memory, as well as a pure detector, e.g. PIN diode, phototransistor, are possible.

Such a highly integrated reflective sensor can be formed as a chip-scale package (CSP). The chip-scale package is a semiconductor device with a housing of the dimension of the first semiconductor body. The sensor is suitable for all applications of reflective optical measurement. In particular, this makes possible extremely compact proximity and gesture sensors and sensors for the measurement of heart rate or other body functions.

The electrical connection between the first and second semiconductor body can be made by flip-chip contacting in which the second semiconductor body comprises contacts facing the first semiconductor body and are connected to contacts of the first semiconductor body.

Within the second semiconductor body arranged at the top side of the semiconductor device, a structure applied after it has been placed can run at the top side of the second semiconductor body, by which it is contacted, for example. Such a second semiconductor body may comprise a radiation-transmissive electrically conductive layer on its side facing away from the first semiconductor body. A conductor structure extends from the top side of the first semiconductor body to the side of the second semiconductor body facing away from the first semiconductor body. However, the conductor structure applied for contacting advantageously does not cover the entire top side of the second semiconductor body, but leaves a part free to allow irradiation.

There may be a depression in the substrate into which the second semiconductor body is inserted in an at least partly sunk manner. This allows production of an even flatter semiconductor component. The side walls of the depression can be mirrored to reduce crosstalk to the first active zone.

The first semiconductor body may comprise contacts on its underside to connect and control the semiconductor device. By these contacts, the semiconductor device can be integrated into a system, for example, a mobile phone by SMT technology.

FIG. 1 shows a schematic view of an example of a semiconductor device. It comprises a first semiconductor body 1 and a second semiconductor body 2. Semiconductor bodies can also be called chips.

The first semiconductor body 1 comprises a substrate 10 and an integrated circuit with an active zone 11 that receives radiation. In this example, the first semiconductor body 1 is a silicon chip with silicon as substrate. The substrate 10 has typically a thickness of 150 µm and serves as a carrier for integrated analog or digital electronics.

The substrate 10 has a top side 15 and an underside 16. The active zone 11 is arranged at the top side 15 as a light-sensitive region on the silicon chip. This can be an implanted PIN diode or a phototransistor, for example. Optionally, a dielectric filter can be provided additionally for wavelength selectivity.

The first semiconductor body 1 is not only a chip that provides the electrical functionality of the circuitry integrated thereon, but also serves as a carrier for the second semiconductor body 2.

The second semiconductor body 2 with an active zone 21 that emits radiation is arranged on the top side 15 of the first semiconductor body 1. In this example, the second semiconductor body 2 is a surface-emitting LED chip electrically conductively connected to the first semiconductor body 1. The thickness of the second semiconductor body 2 is significantly smaller than the thickness of the substrate 10. Due to its small thickness of a few microns such an LED chip is also called a thin-film LED.

The second semiconductor body 2 can be electrically conductively connected to the first semiconductor body 1, for example, by contacts on its side facing the first semiconductor body 1. But also a contacting via contacts on its side facing away from the first semiconductor body 1 is plausible. In such an example, the contacting can be made via conductor structures applied after the second semiconductor body 2 has been placed. Contacts can also be provided both on the side facing the first semiconductor body 1 and the side facing away from the first semiconductor body 1, in the simplest structure one each at the top and at the bottom.

Furthermore, the semiconductor device comprises electrical contacts 12 arranged on the underside 16 of the first semiconductor body 1. These are used to contact and drive the entire semiconductor component. The electrical contacts 12 can be formed as copper contacts with a gold finish, for example.

Production of the first semiconductor body 1 is performed for a plurality of first semiconductor bodies 1 simultaneously and in (wafer) assemblage. This kind of production conducts process steps for the production of the plurality of first semiconductor bodies 1 in parallel for all first semiconductor bodies 1 simultaneously while they are still connected to each other. These process steps include in particular application or growth of layers and structures and, if necessary, also their partial removal to form the integrated circuit with the active zone 11. Only in a final step, the first semiconductor bodies 1 are singulated and isolated from each other.

In the course of the production, the second semiconductor bodies 2 are placed on the first semiconductor bodies 1 in a parallel placement process and connect to each other as long as the latter are still in the assemblage. This placement is carried out simultaneously for all first semiconductor bodies 1 in the assemblage by transferring a plurality of second semiconductor bodies 2 from a sacrificial wafer 52 to the target wafer 54 with the first semiconductor bodies 1 by an elastomer stamp and placing them on the target wafer 54 such that the second semiconductor bodies 2 are arranged at their intended positions on the first semiconductor bodies 1. The stamp plate has a structure that corresponds to the size and positions of the second semiconductor bodies 2 on the target wafer 54.

Production of the second semiconductor bodies 2 is also carried out in parallel in a wafer assemblage. The corresponding wafer is called sacrificial wafer 52. However, the second semiconductor bodies 2 are not singulated by separating the wafer 52. Rather, the second semiconductor bodies 2 are produced simultaneously on a sacrificial layer such that all later second semiconductor bodies 2 are connected to each other via holding structures 30. At the end of the so-called front-end of line (FE) fabrication, the sacrificial layer is removed, for example, by dry chemical etching so that the individual second semiconductor bodies 2 are only connected to each other and the wafer substrate via the holding structures 30, wherein free-standing webs 32 connect the second semiconductor bodies 2 to an anchor structure 34, which in turn connects to the wafer substrate. The second semiconductor bodies 2 produced in this way are arranged in a grid pattern in the assemblage.

The thickness of chips produced in this way can be significantly smaller than in conventionally singulated chips and can be a few microns.

During parallel transfer, the stamp is pressed onto the second semiconductor bodies 2 to be transferred so that they adhere to the stamp. As soon as the stamp moves in the opposite direction, the second semiconductor bodies 2 are separated from the holding structures 30 by the webs 32 or their beginnings at the second semiconductor body 2 tearing off. At the second semiconductor body 2, a tear-off point 40 remains, which may be located at a web-shaped extension 38, which is part of the web of the holding structure 30.

Figure 2A:
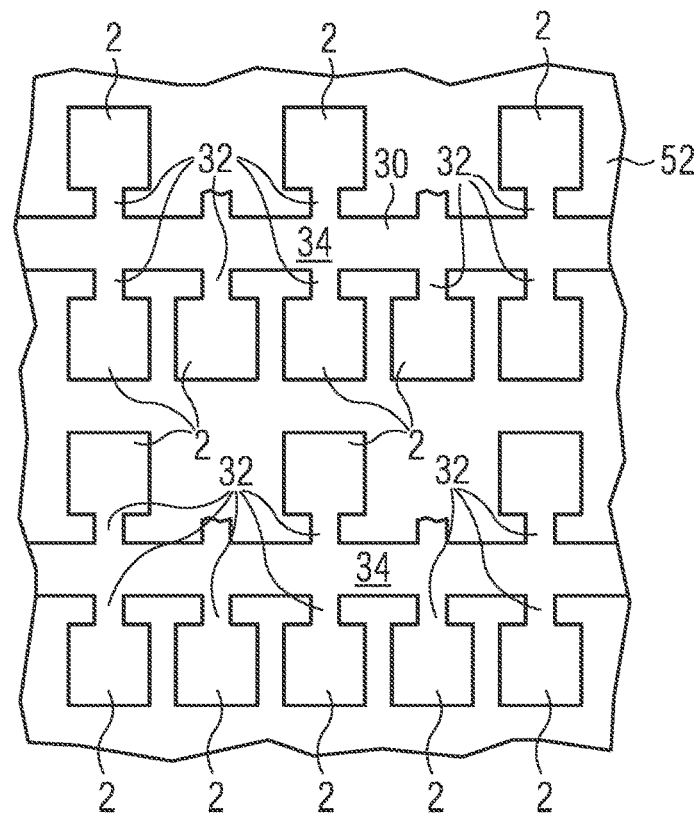
FIG. 2a shows a schematic view of a plurality of second semiconductor bodies connected to each other by a holding structure.
Figure 2B:
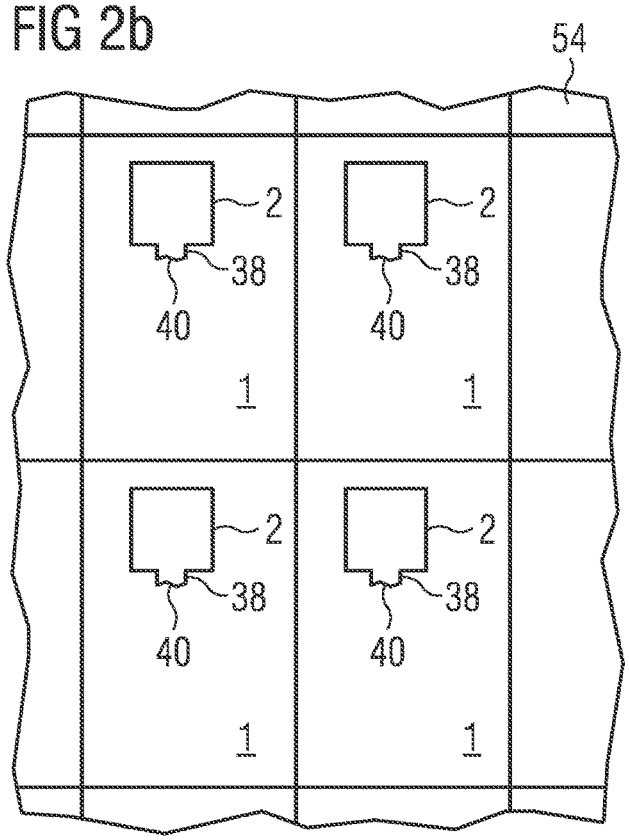
FIG. 2b shows a schematic view of a plurality of second semiconductor bodies arranged on first semiconductor bodies in an assemblage.

FIG. 2a shows a schematic view of the sacrificial wafer 52 comprising a plurality of second semiconductor bodies 2 and the holding structure 30. The second semiconductor bodies 2 are self-supporting after removal of the sacrificial layer and are connected only via webs 32 to an anchor structure 34, which forms the connection between holding structure 30 and wafer substrate. FIG. 2b shows a schematic view of the target wafer 54 comprising a plurality of first semiconductor bodies 1 in the assemblage.

A second semiconductor body 2 has already been placed on each of the first semiconductor bodies 1, wherein the second semiconductor bodies 2 have been removed from the sacrificial wafer 52 corresponding to their position on the target wafer 54 and have been transferred to the target wafer 54 by the stamp.

In the detached second semiconductor body 2, the tear-off point 40 is located at a web-shaped extension 38, which is part of the original web 32. Alternatively, the tear-off point 40 can also be located directly at an outer side of the second semiconductor body 2.

In the parallel placement process, a plurality of second semiconductor bodies 2 are simultaneously transferred by breaking the chips to be transferred out of the sacrificial wafer 52 on contact with the stamp and placing them on the target wafer 54 after the transfer. Then further process steps can be carried out at wafer level, for example, application of an electrical contacting, optical filters, optical barriers, lenses or reflectors. The contacts 12 may also only be opened or defined at the end of the process chain.

Completion of the semiconductor device is carried out in an assemblage so that all available FE processes can be used. In particular, dielectric coatings can be applied spatially selectively, for example, to influence the spectral line sensitivity of the device. Finally, the semiconductor devices are singulated, for example, by a laser or dry chemical process.

Parallel transfer reduces costs compared to serial placement. The parallel placement process described above is also known as transfer printing.

The semiconductor devices manufactured in this way have a very small thickness compared to conventional devices, as neither a printed circuit board nor bonding wire are required. The substrate 10 of the first semiconductor body 1, which must have sufficient mechanical stability, makes the main contribution to the device thickness. It is thus possible to manufacture semiconductor devices whose total thickness is approx. 200 µm, in particular less than 200 µm.

Figure 3:
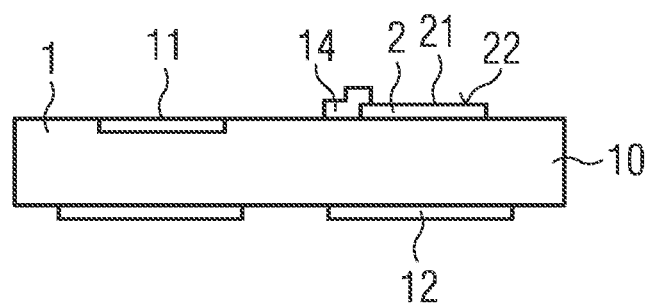
FIG. 3 shows a schematic view of a further example of a semiconductor device.

FIG. 3 shows a schematic view of an example of a semiconductor device. To avoid repetitions, only the differences to the example in FIG. 1 are described.

The second semiconductor body 2 is a surface emitting LED chip with one contact each on its top side and underside. The second semiconductor body 2 comprises a thin, conductive layer 22 that contacts the top side of the second semiconductor body 2 while simultaneously transmitting light. Such a layer 22 may be formed of a transparent electrically conducting oxide (TCO), in particular indium tin oxide (ITO).

A conductor structure 14 extends from the top side of the first semiconductor body 1 to the side of the second semiconductor body 2 facing away from the first semiconductor body 1 to establish an electrically conductive connection between the semiconductor bodies 1, 2. Such a conductor structure 14 can be formed by a suitable process after the second semiconductor body 2 has been placed on as long as the first semiconductor body 1 is still in the wafer composite. To not influence the irradiation excessively, the conductor structure 14 extends only over a partial region of the top side of the second semiconductor body 2.

Figure 4:
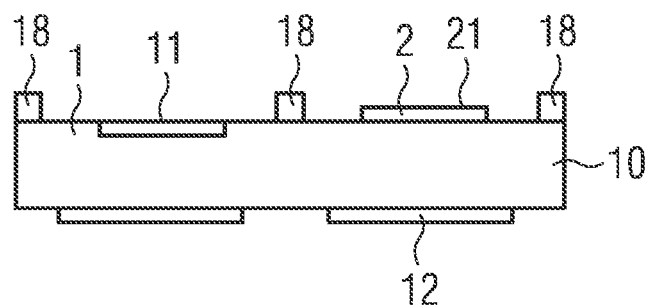
FIG. 4 shows a schematic view of a further example of a semiconductor device.

FIG. 4 shows a schematic view of an example of a semiconductor device. To avoid repetitions, only the differences to the example in FIG. 1 are described. Nevertheless, contacting the second semiconductor body 2 with the first semiconductor body 1 can be carried out as described in connection with FIG. 3. In that example, the second semiconductor body 2 comprises a thin conductive layer 22 to contact the top side of the second semiconductor body 2 and simultaneous transmission for light.

In this example, an optical barrier 18 is provided between the active zones 11, 21 on the first and second semiconductor bodies 1, 2, the optical barrier 18 being supposed to prevent direct irradiation on the active zone 11 of the first semiconductor element 1 along the device surface. The optical barrier can be formed as a rod-shaped dielectric structured layer that serves as an optical separation between the active zones 11, 21. To prevent lateral irradiation, frame-shaped optical barriers 18 can be provided around the active zones 11, 21 so that essentially the reflected emitted radiation of the second semiconductor body 2 is detected. In other words, it is detected to what extent the emitted light is reflected. Such barriers 18 can be produced as dielectric layer structures still in the wafer composite.

This design supports the use of the semiconductor device as a reflective optical measuring sensor. Such a highly integrated reflective sensor can be formed as chip-scale Package (CSP). This makes it possible to produce extremely compact proximity or gesture sensors, sensors for measuring heart rate or other body functions.

Figure 5:
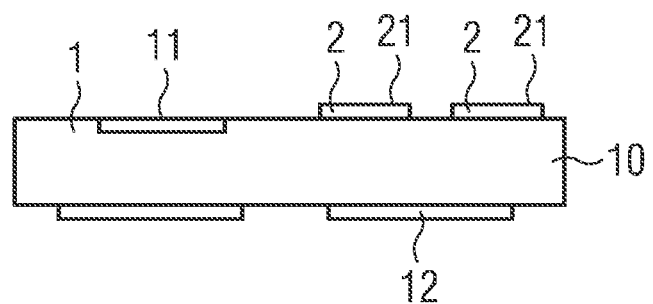
FIG. 5 shows a schematic view of a further example of a semiconductor device.

FIG. 5 shows a schematic view of an example of a semiconductor device. To avoid repetitions, only the differences to the example in FIG. 1 are described.

In this example, two second semiconductor bodies 2 are arranged on the first semiconductor component 1. These can be applied during the same parallel transfer step.

Provision of two second semiconductor bodies 2 allows light of different or equal wavelengths to be emitted. It is also possible to provide a semiconductor device with more than two second semiconductor bodies 2.

Contacting the two second semiconductor bodies 2 with the first semiconductor body can be carried out as described in connection with FIG. 1 or 3, wherein the second semiconductor bodies 2 comprise with each a contact at the top and bottom a thin conductive layer 22 to contact the top side of the second semiconductor bodies 2 with simultaneous transmission for light. Optical barriers 18 can be provided as an option.

Figure 6:
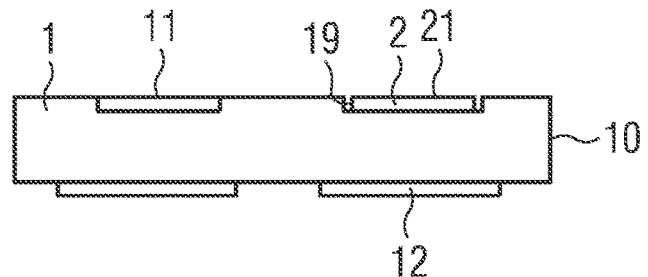
FIG. 6 shows a schematic view of a further example of a semiconductor device.

FIG. 6 shows a schematic view of an example of a semiconductor device. To avoid repetitions, only the differences to the example in FIG. 1 are described.

In this example, the first semiconductor body 1 comprises a depression 19 that may be formed as a recess etched into the silicon chip, for example. During parallel transfer, the second semiconductor body 2 is placed in the depression 19 and electrically connected at its underside. The recess prevents crosstalk from laterally emitting light to the first semiconductor body 1 serving as a detector so that an optical barrier 18 can, but does not have to, be, dispensed with.

Contacting the second semiconductor body 2 with the first semiconductor body can be done as described in connection with FIG. 1 or 3, wherein the second semiconductor body 2 with a contact at the top side and underside comprises a thin conductive layer 22 that contacts the top side of the second semiconductor body 2 with simultaneous transmission for light.

Figure 7:
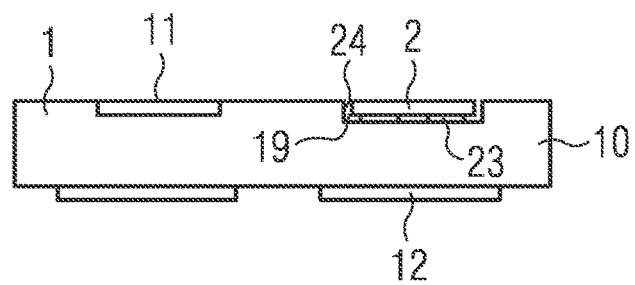
FIG. 7 shows a schematic view of a further example of a semiconductor device.

FIG. 7 shows a schematic view of an example of a semiconductor device. To avoid repetitions, only the differences to the example in FIG. 6 are described.

The second semiconductor body 2 is an LED chip with contacts 23 on its underside. The connection to the first semiconductor body 1 is made by flip-chip contacting. For this purpose, the second semiconductor body 2 is placed by parallel transfer into the recess with mirrored side walls 24 that has been previously etched into the silicon substrate 10, and is electrically connected. The second semiconductor body 2 comprises two contacts 23 on its side facing the first semiconductor body 1 and is mounted without any further connecting wires. To connect the chips electrically, soldering, conductive bonding or pressure welding can be used as joining methods.

The recess 19 comprising a mirror coating 24 improves outcoupling and prevents crosstalk from light emitted laterally to the detector.

Figure 8:
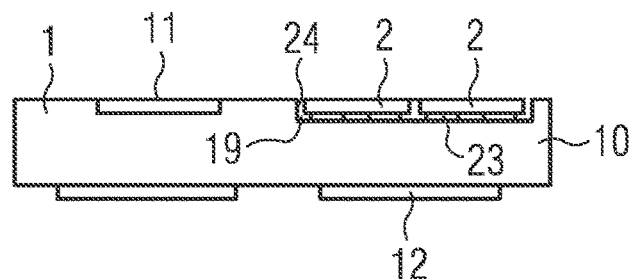
FIG. 8 shows a schematic view of a further example of a semiconductor device.

FIG. 8 shows a schematic view of an example of a semiconductor device. To avoid repetitions, only the differences to the example in FIG. 7 are described.

This example comprises two LED flip chips, as described in connection with FIG. 7, as second semiconductor bodies 2 in the depression 19 with mirrored side walls 24.

Figure 9:
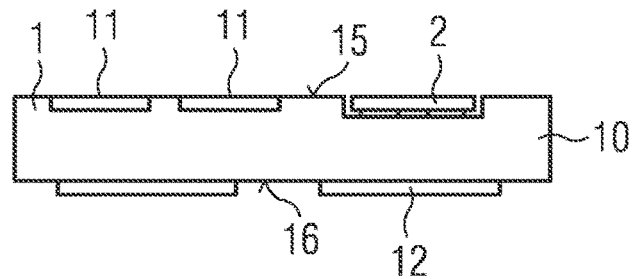
FIG. 9 shows a schematic view of a further example of a semiconductor device.

FIG. 9 shows a schematic view of an example of a semiconductor device. To avoid repetitions, only the differences to the example in FIG. 7 are described.

This example comprises several light-sensitive regions as active zones 11 on the top side 15 of the first semiconductor body 1. They have different spectral sensitivities. They can be broadband, for example, or they can be based on the brightness sensitivity curve $V(\lambda)$, i.e. the spectral brightness sensitivity of the human eye in daylight, or they can serve as daylight barriers.

The features of the examples can be combined. Our devices are not limited by the description based on the examples. Rather, this disclosure comprises any new feature as well as any combination of features including in particular any combination of features in the appended claims, even if the feature or combination itself is not explicitly stated in the claims or examples.

This application claims priority of DE 102017124319.4, the subject matter of which is incorporated herein by reference.

The invention claimed is:

1. A semiconductor device comprising:
   a first semiconductor body comprising a substrate having a first thickness, wherein
   the first semiconductor body comprises a first active zone that generates or receives radiation,
   a second semiconductor body having a second thickness smaller than the first thickness and comprising a tear-off point is arranged on the substrate and connected in an electrically conducting manner to the first semiconductor body, and
   a depression in the substrate into which the second semiconductor body is inserted in an at least partly sunk manner,
   wherein the first active zone is arranged at a raised portion of the substrate, and the raised portion laterally delimits the depression,
   the second semiconductor body comprises a second active zone that generates or receives radiation, the second active zone generates radiation and the first active zone detects the radiation, and the first semiconductor body comprises contacts on its underside for connection to the semiconductor device, side walls of the depression are mirrored, and the depression comprises a mirror coating at the mirrored side walls that reduces crosstalk to the first active zone and replaces an optical barrier.

2. The semiconductor device according to claim 1, wherein the first semiconductor body has a top side at which the first active zone is arranged and on or at which the second semiconductor body is arranged.

3. The semiconductor device according to claim 1, wherein the second semiconductor body comprises contacts connected to contacts of the first semiconductor body by flip-chip contacting.

4. The semiconductor device according to claim 1, wherein the first thickness is less than or equal to 200 μm.

5. The semiconductor device according to claim 1, wherein the first semiconductor body is a silicon chip.

6. The semiconductor device according to claim 1, wherein the second semiconductor body comprises a radiation-transmissive electrically conductive layer on a side remote from the first semiconductor body.

7. The semiconductor device according to claim 1, wherein a conductor structure extends from the first semiconductor body to a side of the second semiconductor body remote from the first semiconductor body.

8. The semiconductor device according to claim 1, wherein the second semiconductor body comprises a web-shaped extension having the tear-off point at its end.

9. The semiconductor device according to claim 1, wherein the second semiconductor body is a thin-film LED.

10. A sensor comprising a semiconductor device according to claim 1, wherein the sensor is a proximity, gesture, heart rate or body function sensor.

* * * * *